United States Patent
Cavazza

(10) Patent No.: US 6,217,898 B1
(45) Date of Patent: *Apr. 17, 2001

(54) PHARMACEUTICAL COMPOSITION COMPRISING CARNITINE OR ALKANOYL L-CARNITINE, FOR THE PREVENTION AND TREATMENT OF DISEASES BROUGHT ABOUT BY LIPID METABOLISM DISORDERS

(75) Inventor: Claudio Cavazza, Rome (IT)

(73) Assignee: Sigma-Tau HealthScience S.p.A., Pomezia (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/042,646

(22) Filed: Mar. 17, 1998

Related U.S. Application Data

(63) Continuation of application No. 08/758,460, filed on Nov. 29, 1996.

(51) Int. Cl.$^7$ .............................. A61K 9/127; A61K 9/08; A61K 9/20; A61K 9/48; A61K 47/12
(52) U.S. Cl. ..................... 424/450; 424/451; 424/464; 424/489; 514/557; 514/824
(58) Field of Search .................................. 424/400, 450, 424/451, 464, 489; 514/557, 824

(56) References Cited

U.S. PATENT DOCUMENTS

| | | |
|---|---|---|
| 3,810,994 | 5/1974 | Wiegand . |
| 4,255,449 | 3/1981 | Cavazza . |
| 4,268,524 | 5/1981 | Cavazza . |
| 4,464,393 | 8/1984 | Cavazza . |
| 5,008,288 | 4/1991 | Stracher . |
| 5,030,657 | 7/1991 | Burtle . |
| 5,037,851 | 8/1991 | Cavazza . |
| 5,039,698 | 8/1991 | Leung . |
| 5,043,355 | 8/1991 | Cavazza . |
| 5,145,871 | 9/1992 | Cavazza . |
| 5,173,508 | 12/1992 | Cavazza . |
| 5,192,805 | 3/1993 | Cavazza . |
| 5,227,518 | 7/1993 | Cavazza . |
| 5,270,472 | 12/1993 | Taglialatela et al. . |
| 5,418,253 | 5/1995 | Cavazza et al. . |
| 5,430,065 | 7/1995 | Cavazza . |
| 5,432,199 | 7/1995 | Cavazza . |
| 5,494,924 | 2/1996 | Cavazza et al. . |
| 5,534,549 | 7/1996 | Tinti et al. . |
| 5,536,506 | 7/1996 | Majeed . |
| 5,536,516 | 7/1996 | Moffett . |
| 5,543,556 | 8/1996 | Tinti et al. . |
| 5,547,986 | 8/1996 | Tinti et al. . |
| 5,591,450 | 1/1997 | Cavazza et al. . |
| 5,614,556 | 3/1997 | Cavazza et al. . |
| 5,626,849 | 5/1997 | Hastings . |
| 5,627,212 | 5/1997 | Cavazza et al. . |
| 5,637,305 | 6/1997 | Cavazza et al. . |
| 5,639,767 | 6/1997 | Cavazza et al. . |

FOREIGN PATENT DOCUMENTS

| | | |
|---|---|---|
| 0 793 962 | 9/1997 | (EP) . |
| 0 808 626 | 11/1997 | (EP) . |

OTHER PUBLICATIONS

Weiner in *Drug Development and Industrial Pharmacy*, vol. 15(10), pp. 1523–1556 (1989).
Y.L. Lewis et al, *Phytochemistry*, vol. 4, 619 (1965).
A. Streenivasan, *Current Science*, vol. 4, p. 151, (1959).
Y. Bremer, *TIBS*, vol. 2, p. 207 (1977).
J. D. McGarry, *J. Biol. Chem.*, vol. 254, p. 8163 (1979).
S. V. Pande, *PNAS USA*, vol. 72, p. 883 (1975).
J. G. Hamilton, *Lipids*, vol. 12, p. 1, (1976).
J. Triscari et al., *Lipids*, vol. 12, p. 357 (1976).
J. A. Watson, *Arch. Biochem. Biophys.*, vol. 135, p. 209 (1969).
J. M. Lowenstein *J. Biol Chem.*, vol. 246, p. 629 (1971).
R. L. Hood, *Comp. Biochemical Physiol.*, vol. 81B, p. 667 (1985).
L. A. Carlson, *J. Atheroscler. Res.*, vol. 8, p. 667 (1968).
L. A. Carlson, *Atheroschlerosis*, vol. 16, p. 349 (1972).
R.K. Donabedian, *Clin. Chem.*, vol. 20, p. 632 (1974).
C.R. Sirtori, *Atherosclerosis*, vol. 26, p. 78 (1977).

*Primary Examiner*—Gollamudi S. Kishore
(74) *Attorney, Agent, or Firm*—Oblon, Spivak, McClelland, Maier & Neustadt, P.C.

(57) ABSTRACT

A pharmaceutical compositions comprising L-carnitine or alkanoyl L-carnitine and hydroxycitric or pantothenic acid or derivatives thereof for the prevention and treatment of diseases brought about by lipid metabolism disorders, is disclosed.

15 Claims, No Drawings

PHARMACEUTICAL COMPOSITION COMPRISING CARNITINE OR ALKANOYL L-CARNITINE, FOR THE PREVENTION AND TREATMENT OF DISEASES BROUGHT ABOUT BY LIPID METABOLISM DISORDERS

This application is a continuation of U.S. Ser. No. 08/758,460 filed Nov. 29, 1996.

The present invention relates to a novel therapeutic use of L-carnitine, some alkanoyl L-carnitines and the pharmacologically acceptable salts thereof in combination with hydroxycitric or pantothenic acid or derivatives thereof (wherein "derivatives thereof" also encompasses natural products and their extracts containing same) for the prevention and therapeutic treatment of diseases brought about by lipid metabolism disorders, such as cardiovascular disorders, atherosclerosys, hyperlipidaemias and obesity, and for controlling and decreasing the appetite.

According to its broadest aspect the invention relates to the co-ordinated use of L-carnitine or an alkanoyl L-carnitine or the pharmacologically acceptable salts thereof with hydroxycitric or pantothenic acid or derivatives thereof. By "co-ordinated use" of the aforesaid compounds it is meant indifferently either the co-administration, i.e. the substantially concomitant supplementation of L-carnitine or alkanoyl L-carnitine or a pharmacologically acceptable salt thereof and hydroxycitric or pantothenic acid or a derivative thereof, as active ingredients, or the administration of a combination preparation comprising a mixture of the aforesaid active ingredients, in addition to suitable excipients, if any.

The present invention also relates to orally, parenterally, rectally or transdermally administrable pharmaceutical compositions suitable for treating the aforesaid disorders and for controlling and decreasing the appetite, which comprise, as active ingredients, L-carnitine or an alkanoyl L-carnitine or a pharmacologically acceptable salt thereof and hydroxycitric acid or pantothenic acid or derivative thereof. Preferred hydroxycitric acid derivatives are the salts and esters thereof and the natural products and their extracts containing same, as specified in more detail hereinbelow. It should be understood that whenever in the present specification reference is made for the sake of simplicity to "hydroxycitric acid", the naturally occurring compound, i.e (−)-treo hydroxycitric acid, is meant.

Preferred pantothenic acid derivatives comprise 4'-phospho-pantothenate, 4'-phosphopantothenylcisteine, 4'-phosphopantotheine, pantotheine and pantethine. Pantethine is particularly preferred.

Hydroxycitric acid and derivatives thereof may occur as extracts of natural products containing hydroxycitric acid at high concentrations, such as the extract of the fruits of Garcinia (Garcinia cambodia, Garcinia atroviridis, Garcinia indica, Garcinia citrin), of the fruits of Malabar Tamarind or Gorikapuli (Lewis Y. L., Neelakantan S., Phyto-chemistry 4, 619, 1965), (Streenivasan A., Vankataraman R., Current Science 4, 151, 1959) or other extract of natural products containing same.

A preferred salt of hydroxycitric acid is calcium hydroxycitrate.

The alkanoyl L-carnitines useful for the novel therapeutic use of the present invention are those wherein the alkanoyl group is a straight or branched group, having from 2 to 8 carbon atoms, preferably from 2 to 6 carbon atoms.

Particularly preferred are acetyl, propionyl, butyryl, valeryl and isovaleryl L-carnitine.

Pharmaceutically acceptable salts of L-carnitine or alkanoyl L-carnitine include, in addition to the inner salts, any salt of these with acids which do not give rise to undesired or side effects. The formation of pharmaceutically acceptable acid addition salt is well known to the experts in pharmacy and pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

Previous therapeutic uses of L-carnitine are already known.

For instance L-carnitine has been used in the cardiovascular field in the treatment of acute and chronic myocardial ischaemia, angina pectoris, cardiac arrhythmias and insufficiency, and peripheral vascular diseases.

In nephrology, L-carnitine has been administered to chronic uraemic patients who are subjected to regular haemodialysis treatment with a view to counteracting muscular asthenia and the onset of muscular cramps.

Moreover, U.S. Pat. No. 3,810,994 (Ethyl Corporation) discloses the therapeutic utility of pharmaceutical compositions of L-carnitine or salts or esters thereof, for the treatment of obesity.

U.S. Pat. No. 4,255,449 (Cavazza) and U.S. Pat. No. 4,268,524 (Cavazza) disclose the use of L-carnitine and alkanoyl L-carnitine to normalize the abnormal ratio between low density lipoprotein (LDL)+very low density lipoproteins (VLDL) and high density lipoprotein (HDL) which is an aetiological factor for various cardiovascular diseases.

As known, through the beta-oxidation of fatty acids L-carnitine is capable of preventing their accumulation and of supplying the energy requirement of cells (Bremer Y., TIBS 2, 207, 1977) via modulation of extra- and intramitochondrial CoA.

The carnitine pool not only regulates the bio-oxidation of intramitochondrial fatty acids, but also inhibits the formation of triglycerides (Bieber L. L., J. Biol. Chem. 254, 8163, 1979; Pande D. V., Proc. Nat. Acad. Sci. USA 72, 883, 1975).

Hydroxycitric acid, too, has for some time now been known as a metabolic factor. It is present, in fact, in large amounts in a number of plants used as foodstuffs and, in particular, in Malabar Tamarind and in the fruits of various species of Garcinia and its extraction and isolation have permitted extensive biochemical and pharmacological study of the substance. Recent data have revealed its importance as a regulator of the synthesis of cholesterol and fatty acids (Hamilton Y. G., Lipids 12, 1, 1976).

Hydroxycitric acid is capable of inhibiting the activity of ATP-citratolyase, an enzyme which catalyses the extramitochondrial conversion of citrates to oxoacetates and acetyl Coenzyme A.

The importance of this enzyme consists in its ability to maintain the Coenzyme A pool necessary for lipid and cholesterol synthesis. The enzymatic reaction catalysed by citratolyase which leads to the synthesis of cholesterol and fatty acids from carbohydrates is inhibited by hydroxycitric acid which together with the reduction in lipid synthesis also leads to a greater storage of carbohydrates in the form of glycogen in the liver (Berkbout T. A., Biochem. J. 48, 6, 1990; Triscari Y., Sullivan A. C., Lipids 12, 357, 1976; Watson Y. A., Fang M., Arch. Biochem. Biophys. 135, 209, 1969).

Both L-carnitine and hydroxycitric acid are, therefore, capable of exerting an action upon lipid metabolism via different mechanisms: on the one hand, L-carnitine facilitates the oxidation and intramitochondrial utilization of fatty acids and prevents the accumulation of triglycerides, and, on the other, hydroxycitric acid prevents their actual synthesis (Lowenstein Y. M., J. Biol. Chem. 246, 629, 1971; Hood R. L., Comp. Biochemical Physiol. 81B, 667, 1985).

What have proved very surprising and unexpected, however, are the synergistic effects which can be obtained on energy metabolism and on lipid metabolism by combining these two compounds or by co-ordinately administering them.

This unexpected synergistic effect obtained by the co-ordinated use of L-carnitine or its derivatives and hydroxycitric or pantothenic acid or derivatives thereof has been demonstrated in numerous studies, so much so, indeed, as to suggest that this combination can be used to advantage in facilitating the elimination of lipids and cholesterol from tissues, in the treatment of cardiovascular diseases, and in preventing abnormal formation and accumulation of fats.

The research conducted to date has shown that the co-ordinated use of the two compounds proves surprisingly effective in inhibiting the formation of atherosclerosis and the infiltration of tissues, as well as the formation of cholesterol and triglycerides.

In addition to the anticholesterolaemic and antidyslipidaemic effects induced by this combination, the research has also revealed a reduction of appetite and reduced food consumption with consequent weight loss.

This new pharmaceutical composition can, therefore, be used in the prevention and treatment of all those disease conditions related to a high concentration of cholesterol and lipids in the tissues, such as, for instance, atherosclerosis, hypercholesterolaemia, and cardiovascular diseases, and in the treatment of obesity.

The toxicological results are reported below, as are the results of the most significant studies in terms of evidence of the surprising synergistic effect that can be obtained with a combination of L-carnitine or one of its derivatives and hydroxycitric acid or one of its derivatives. The data reported in these studies demonstrate the unexpected potentiation of action obtainable with this new composition and that important practical applications stem from this activity in the pharmaceutical, dietary and alimentary fields for the prevention or therapy of numerous disease conditions related to lipid metabolism disorders, such as atherosclerosis, hypercholesterolaemia, obesity and cardiovascular diseases.

Toxicology

The tests performed, administering a combination of L-carnitine or its derivatives and calcium hydroxycitrate or an extract from *Garcinia cambogia* (with a roughly 30% hydroxycitrate concentration) in a single dose at high concentrations, have demonstrated the good tolerability of the new composition. High doses of L-carnitine or its derivatives (1 g/kg) could be administered, in fact, together with high doses of calcium hydroxycitrate (up to and above 1 g/kg) or of *Garcinia cambogia* hydroxycitrate extract (2 g/kg), orally to Wistar rats, without any evidence of signs of toxicity related to the administration of any of the various presentation forms which the composition according to the invention can take on. The good tolerability of the composition has also been established through prolonged oral administration of the product together with the diet for three consecutive months in both male Wistar rats and in mice.

Tests in Experimentally Obese Rats

Male Wistar rats aged about 2 months were fed on a lipogenic diet (50% glucose, 20% casein, 4% cellulose, 5% salt mixture, 1% hazel nut oil, 18% starch, 1% vitamin mixture).

This diet was administered for fifteen days consecutively to different groups of rats, one of which served as a control group, whereas in the other groups the diet was administered together with calcium hydroxycitrate (1%–2%) or *Garcinia cambogia* extract (2%–4%) or L-carnitine (2%–4%) or acetyl L-carnitine or propionyl L-carnitine at the same doses, or together with various combinations of these products at the same doses. At the end of the fifteenth day of treatment, food consumption was evaluated in treated rats vs. controls and increases in body weight and in serum triglycerides and epididymal fat were measured.

Food Consumption Results

During the fifteen days of treatment on a lipogenic diet a substantial reduction in daily food consumption was detected in the animals treated with calcium hydroxycitrate or with *Garcinia cambogia* extract. No changes compared to controls were noted, on the other hand, in rats treated with L-carnitine, propionyl L-carnitine or acetyl L-carnitine. The reduction in food consumption was, however, much more marked in the group of animals treated with the combination of calcium hydroxycitrate plus L-carnitine, acetyl L-carnitine, and particularly propionyl L-carnitine, even as compared to that detected in the rats treated with calcium hydroxycitrate or *Garcinia cambogia* extract.

Whereas, with the largest dose of calcium hydroxycitrate, the daily food consumption dropped from an initial values of 18.8 g to a value of 15.1 g after fifteen days' treatment, the respective values for the lower dose were 19.2 g and 17.1 g.

The non-significant changes detected with the two doses of L-carnitine, acetyl L-carnitine and propionyl L-carnitine become highly significant when these products are combined even with the lower doses of calcium hydroxycitrate or *Garcinia cambogia* extract.

In the animals treated with the combination of calcium hydroxycitrate and propionyl L-carnitine at the lower doses, this leads, for example, to a reduction in food consumption from 18.4 g to 13.2 g, thus demonstrating a potentiation of the effect on the reduction of food intake. A similar, though more limited, degree of potentiation is observed in the data for the combination of the various carnitines with *Garcinia cambogia* extract (Table 1).

Body Weight Results

Body weight gain is also reduced by the administration of calcium hydroxycitrate in correlation with the dose administered. In these tests, too, while no significant changes are detectable with the administration of carnitines alone, highly significant changes are observed when the carnitines are combined with calcium hydroxycitrate or with *Garcinia cambogia* extract. In the group of animals treated with the combination of calcium hydroxycitrate plus carnitines, the reduction in body weight gain is much greater than that obtainable with administration of the highest dose of calcium hydroxycitrate alone (Table 2).

Serum Triglyceride and Epididymal Fat Results

The potent synergistic effect between carnitines and calcium hydroxycitrate or *Garcinia cambogia* extract is clearly demonstrated by the results regarding serum triglyceride and epididymal fat values in rats on a lipogenic diet. After fifteen days of treatment a powerful effect in terms of a reduction in both parameters was detectable, in fact, in the group of animals treated with the combination of carnitines plus calcium hydroxycitrate or *Garcinia cambogia* extract.

Among the carnitines, the most effective was propionyl L-carnitine, which, when combined with calcium hydroxycitrate, maintains both serum triglycerides and epididymal fats practically within normal levels (Table 3).

Experimental Hypertrigyceridaemia Tests

In these tests, male Wistar rats serum triglyceride elevation was induced experimentally by means of the oral administration of fructose according to the method disclosed by L. A. V. Carlson (J. Atheroscler. Res. 8, 667, 1968; Atherosclerosis 16, 349, 1972). In the 5-day period prior to administration of 3 g of fructose, the rats, divided into groups, were treated with L-carnitine or its derivatives or with calcium hydroxycitrate or *Garcinia cambogia* extract at different doses, or with various combinations of these products.

The administration of these products was then repeated two hours after administration of fructose, and 5 hours later all animals were sacrificed. Triglyceride assay was then performed according to the method of R. K. Donabedian (Clin. Chem 20, 632, 1974). The results obtained in these tests demonstrate that the fructose-induced hypertriglyceridaemia is not modified by the administration of carnitines, whereas it is reduced by the administration of calcium hydroxycitrate or *Garcinia cambogia* extract. The hypertriglyceridaemia-reducing effect is, however, substantially increased and potentiated when the calcium hydroxycitrate or *Garcinia cambogia* extract is combined with the carnitines. The potentiating effect is marked for all carnitines, but most notably in the case of propionyl L-carnitine.

Experimental Atherosclerosis Tests

Also in atherosclerotic vascular lesions induced experimentally according to the method of M. R. Malinow (Atherosclerosis 48, 105, 1983), with administration of an atherogenic diet (24% casein, 10% cotton oil, 5% salt, 60% sugar, 1% cholesterol, Vit $D_2$ 200 mUST/g of diet) for six weeks consecutively to different groups of male Wistar rats, it has been shown that the combination of carnitines plus calcium hydroxycitrate or *Garcinia cambogia* extract is capable of substantially potentiating the anti-atherogenic effect.

This was assessed by measuring the thickness of the abdominal aorta and the intensity of staining induced by Sudan IV using a scoring system from 1 to 5, according to degree of severity. By means of this assessment, it was clearly demonstrated that both L-carnitine and calcium hydroxycitrate or *Garcinia cambogia* extract are capable of reducing the severity of the atherosclerotic lesions. The incidence of these lesions, however, is substantially inhibited to the point of complete elimination in the groups of animals treated with a combination of these products.

The incidence of atherosclerotic lesions was completely inhibited particularly with the combination of calcium hydroxycitrate and propionyl L-carnitine. These tests, too, therefore, demonstrate the intense synergistic action of carnitines and calcium hydroxycitrate.

Experimental Hypercholesterolaemia Tests

The results of tests conducted in Wistar rats with hypercholesterolaemia induced by diet according to the method described by C. R. Sirtori (Atherosclerosis 26, 78, 1977) also confirm the surprisingly marked potentiating effect of calcium hydroxycitrate plus carnitines in reducing cholesterol values. Treatment both with L-carnitine and with calcium hydroxycitrate or with *Garcinia cambogia* extract, or with a combination of these products, was initiated together with a hypercholesterolaemia-inducing diet and continued for six weeks consecutively. At the end of this period, the assay was performed on the serum of the control animals and on that of the treated animals according to the method described by P. Roschlan (Clin. Chem. Clin. Biochem. 12, 403, 1975). The total cholesterol values observed showed a fair degree of lowering induced both by the treatment with calcium hydroxycitrate and by the treatment with *Garcinia cambogia* extract. Practically normal cholesterolaemia values were restored in the animals treated with the combination of calcium hydroxycitrate plus carnitines, thus demonstrating a marked synergistic effect between these two compounds characterizing the novel composition according to the present invention.

The following non-limiting examples illustrate some compositions according to the present invention.

EXAMPLES

1) L-carnitine . . . mg 500
   Calcium hydroxycitrate . . . mg 300
2) Acetyl L-carnitine . . . mg 500
   Calcium hydroxycitrate . . . mg 300
3) Propionyl L-carnitine . . . mg 500
   Calcium hydroxycitrate . . . mg 300
4) Isovaleryl L-carnitine . . . mg 500
   Calcium hydroxycitrate . . . mg 300
5) Valeryl L-carnitine . . . mg 500
   Calcium hydroxycitrate . . . mg 300
6) Butyryl L-carnitine . . . mg 500
   Calcium hydroxycitrate . . . mg 300
7) L-carnitine . . . mg 500
   *Garcinia cambodia* extract mg 500
   (30% hydroxycitric acid)
8) Acetyl L-carnitine . . . mg 500
   *Garcinia cambodia* extract mg 500
   (30% hydroxycitric acid)
9) Propionyl L-carnitine . . . mg 500
   *Garcinia cambodia* extract mg 500
   (30% hydroxycitric acid)
10) Isovaleryl L-carnitine . . . mg 500
    *Garcinia cambodia* extract mg 500
    (30% hydroxycitric acid)
11) Valeryl L-carnitine . . . mg 500
    *Garcinia cambodia* extract mg 500
    (30% hydroxycitric acid)
12) Butyryl L-carnitine . . . mg 500
    *Garcinia cambodia* extract mg 500
    (30% hydroxycitric acid)
13) L-carnitine 500 mg, calcium hydroxycitrate 300 mg, Beta carotene 12500 I.V., Vit. $B_2$ 15 mg, Vit. C 100 mg, Vit. $D_3$ 200 I.V., Vit. $B_{12}$ 1.5 mcg, Folic acid 200 mcg, Vit. E 10 mg, Iron (as $FeSO_4$) 32 mg, Manganese (as $MnSO_4$) 5 mg, Zinc (as Zn acetate) 5 mg, Phosphorus (as $Na_2HPO_4$) 25 mg, Molybdenum 7,5 mg, Potassium 7,5 mg, Chromium 15 mcg, Selenium 40 mcg.
14) L-carnitine . . . g 1.223
    pantethine . . . g 0.500
    methyl-p-hydroxybenzoate g 0.015
    sorbitol . . . g 1.000
    sodium saccharinate . . . g 0.060 citric acid . . . g 0.120 sodium hydroxyde . . . g 0.032 bigarade flavour . . . g 0.050 orange flavour . . . g 0.010 pure water, balance to . . . ml 10.0

TABLE I

MEAN DAILY FOOD CONSUMPTION (g) PER ANIMAL

| | Before treatment | After 15 days |
|---|---|---|
| Calcium hydroxycitrate (g 1/100 g diet) | 19.2 ± 0.65 | 17.1 ± 0.35 |
| Calcium hydroxycitrate (g 2/100 g diet) | 18.8 ± 0.44 | 15.1 ± 0.46 |
| L-carnitine (g 2/100 g diet) | 17.3 ± 0.35 | 181.1 ± 0.50 |
| L-carnitine (g 4/100 g diet) | 18.4 ± 0.61 | 17.8 ± 6.41 |
| Acetyl L-carnitine (g 2/100 g diet) | 18.6 ± 0.39 | 18.4 ± 0.44 |
| Acetyl L-carnitine (g 4/100 g diet) | 18.2 ± 0.41 | 18.8 ± 0.57 |
| Proprionyl L-carnitine (g 2/100 g diet) | 17.7 ± 0.56 | 17.1 ± 0.38 |
| Proprionyl L-carnitine (g 4/100 g diet) | 18.2 ± 0.44 | 18.5 ± 0.48 |
| *Garcinia cambodia* (g 4/100 g diet) | 17.9 ± 0.34 | 16.8 ± 0.44 |
| Calcium hydroxycitrate (g 1/100 g diet) + L-carnitine (g 2/100 g diet) | 18.9 ± 0.61 | 14.4 ± 0.50 |
| Calcium hydroxycitrate (g 1/100 g diet) + Acetyl L-carnitine (g 2/100 g diet) | 19.1 ± 0.58 | 14.8 ± 0.64 |
| Calcium hydroxycitrate (g 1/100 g diet) + Propionyl L-carnitine (g 2/100 g diet) | 18.4 ± 0.49 | 13.2 ± 0.53 |
| L-carnitine (g 2/100 g diet) + *Garcinia cambodia* (g 4/100 g diet) | 18.1 ± 4.7 | 15.9 ± 4.1 |
| Acetyl L-carnitine (g 2/100 g diet) + *Garcinia cambodia* (g 4/100 g diet) | 18.8 ± 3.9 | 16.2 ± 4.9 |
| Propionyl L-carnitine (g 2/100 g diet) + *Garcinia cambodia* (g 4/100 g diet) | 18.1 ± 4.8 | 14.4 ± 4.7 |

TABLE 2

BODY WEIGHT INCREASE AFTER 15 DAY-TREATMENT

| | Final body weight increase (g) |
|---|---|
| Controls | 62.8 ± 3.5 |
| Calcium hydroxycitrate (g 1/100 g diet) | 46.6 ± 4.1 |
| Calcium hydroxycitrate (g 2/100 g diet) | 38.9 ± 3.8 |
| L-carnitine (g 2/100 g diet) | 66.2 ± 4.9 |
| L-carnitine (g 4/100 g diet) | 64.5 ± 5.1 |
| Acetyl L-carnitine (g 2/100 g diet) | 60.4 ± 7.1 |
| Acetyl L-carnitine (g 4/100 g diet) | 60.1 ± 6.1 |
| Proprionyl L-carnitine (g 2/100 g diet) | 62.4 ± 3.9 |
| Proprionyl L-carnitine (g 4/100 g diet) | 58.7 ± 3.7 |
| *Garcinia cambodia* (g 4/100 g diet) | 51.4 ± 3.3 |
| Calcium hydroxycitrate (g 1/100 g diet) + L-carnitine (g 2/100 g diet) | 28.7 ± 4.4 |
| Calcium hydroxycitrate (g 1/100 g diet) + Acetyl L-carnitine (g 2/100 g diet) | 31.6 ± 3.9 |
| Calcium hydroxycitrate (g 1/100 g diet) + Propionyl L-carnitine (g 2/100 g diet) | 24.4 ± 2.8 |
| L-carnitine (g 2/100 g diet) + *Garcinia cambodia* (g 4/100 g diet) | 38.6 ± 3.1 |
| Acetyl L-carnitine (g 2/100 g diet) + *Garcinia cambodia* (g 4/100 g diet) | 36.8 ± 4.4 |
| Propionyl L-carnitine (g 2/100 g diet) + *Garcinia cambodia* (g 4/100 g diet) | 34.8 ± 6.5 |

TABLE 3

SERUM TRIGLYCERIDES AND EPIDIDIMAL FAT AFTER 15 DAY-TREATMENT

| | Triglycerides (mg/100 ml) | Epididimal fat (g) |
|---|---|---|
| Controls | 94.68 ± 6.6 | 4.65 ± 0.41 |
| Calcium hydroxycitrate (g 1/100 g diet) | 76.84 ± 6.9 | 3.91 ± 0.36 |
| Calcium hydroxycitrate (g 2/100 g diet) | 73.66 ± 7.1 | 3.32 ± 0.39 |
| L-carnitine (g 2/100 g diet) | 92.55 ± 7.7 | 4.21 ± 4.1 |
| L-carnitine (g 4/100 g diet) | 90.44 ± 6.8 | 4.34 ± 2.9 |
| Acetyl L-carnitine (g 2/100 g diet) | 95.81 ± 8.2 | 4.10 ± 3.8 |
| Acetyl L-carnitine (g 4/100 g diet) | 90.8 ± 7.5 | 4.15 ± 3.5 |
| Proprionyl L-carnitine (g 2/100 g diet) | 88.4 ± 8.16 | 4.19 ± 4.4 |
| Proprionyl L-carnitine (g 4/100 g diet) | 82.7 ± 6.6 | 4.0 ± 5.6 |
| *Garcinia cambodia* (g 4/100 g diet) | 80.4 ± 7.3 | 3.85 ± 3.5 |
| Calcium hydroxycitrate (g 1/100 g diet) + L-carnitine (g 2/100 g diet) | 71.5 ± 6.7 | 3.25 ± 2.9 |
| Calcium hydroxycitrate (g 1/100 g diet) + Acetyl L-carnitine (g 2/100 g diet) | 68.2 ± 5.5 | 3.0 ± 2.7 |
| Calcium hydroxycitrate (g 1/100 g diet) + Propionyl L-carnitine (g 2/100 g diet) | 60.5 ± 7.4 | 2.25 ± 2.2 |
| L-carnitine (g 2/100 g diet) + *Garcinia cambodia* (g 4/100 g diet) | 75.4 ± 3.1 | 3.50 ± 3.1 |

TABLE 3-continued

SERUM TRIGLYCERIDES AND EPIDIDIMAL FAT AFTER 15 DAY-TREATMENT

|  | Triglycerides (mg/100 ml) | Epididimal fat (g) |
|---|---|---|
| Acetyl L-carnitine (g 2/100 g diet) + Garcinia cambodia (g 4/100 g diet) | 72.3 ± 4.4 | 3.25 ± 4.3 |
| Propionyl L-carnitine (g 2/100 g diet) + Garcinia cambodia (g 4/100 g diet) | 70.3 ± 5.6 | 2.95 ± 3.8 |

TABLE 4

TEST ON EXPERIMENTALLY-INDUCED HYPERTRIGYCERIDAEMIA (mg/100 ml)

| Controls | 195.8 ± 9.8 |
|---|---|
| Calcium hydroxycitrate (g 0.5/Kg) | 170.6 ± 8.5 |
| Calcium hydroxycitrate (g 1/Kg) | 145.5 ± 8.5 |
| L-carnitine (g 0.5/Kg) | 190.4 ± 9.6 |
| L-carnitine (g 1/Kg) | 190.8 ± 8.6 |
| Acetyl L-carnitine (g 0.5/Kg) | 191.2 ± 9.1 |
| Acetyl L-carnitine (g 1/Kg) | 188.4 ± 5.5 |
| Propionyl L-carnitine (g 0.5/Kg) | 184.2 ± 6.8 |
| Proprionyl L-carnitine (g 1/Kg) | 180.4 ± 7.9 |
| Garcinia cambodia (g 0.5/Kg) | 170.6 ± 5.4 |
| Calcium hydroxycitrate (g 0.5/Kg) + L-carnitine (g 0.5/Kg) | 125.8 ± 9.1 |
| Calcium hydroxycitrate (g 0.5/Kg) + Acetyl L-carnitine (g 0.5/Kg) | 120.4 ± 8.8 |
| Calcium hydroxycitrate (g 0.5/Kg) + Propionyl L-carnitine (g 0.5/Kg) | 108 ± 9.4 |
| Garcinia cambodia (g 0.5/Kg) + L-carnitine (g 0.5/Kg) | 145.4 ± 8.6 |
| Garcinia cambodia (g 0.5/Kg) + Acetyl L-carnitine (g 0.5/Kg) | 140.4 ± 7.4 |
| Garcinia cambodia (g 0.5/Kg) + Propionyl L-carnitine (g 0.5/Kg) | 125 ± 8.5 |

TABLE 5

TESTS ON EXPERIMENTALLY-INDUCED HYPERCHOLESTEROLEMIA (TOTAL CHOLESTEROL mg/dl)

| Controls | 92.5 ± 4.4 |
|---|---|
| Hypercholesterolemic controls | 270.5 ± 10.4 |
| Calcium hydroxycitrate | 196.6 ± 9.6 |
| Calcium hydroxycitrate (g 1/100 g diet) | 180.5 ± 8.1 |
| L-carnitine (g 2/100 g diet) | 270.4 ± 5.1 |
| L-carnitine (g 4/100 g diet) | 260.6 ± 4.4 |
| Acetyl L-carnitine (g 2/100 g diet) | 266.7 ± 7.7 |
| Acetyl L-carnitine (g 4/100 g diet) | 255.4 ± 9.4 |
| Propionyl L-carnitine (g 2/100 g diet) | 250.6 ± 10.1 |
| Proprionyl L-carnitine (g 4/100 g diet) | 235.3 ± 9.6 |
| Garcinia cambodia (g 4/100 g diet) | 250.7 ± 4.7 |
| Calcium hydroxycitrate (g 1/100 g diet) + L-carnitine (g 2/100 g diet) | 155.8 ± 8.8 |
| Calcium hydroxycitrate (g 1/100 g diet) + Acetyl L-carnitine (g 2/100 g diet) | 150.5 ± 7.1 |
| Calcium hydroxycitrate (g 1/100 g diet) + Propionyl L-carnitine (g 2/100 g diet) | 110.6 ± 6.6 |
| L-carnitine (g 2/100 g diet) + Garcinia cambodia (g 4/100 g diet) | 179.6 ± 9.6 |
| Acetyl L-carnitine (g 2/100 g diet) + Garcinia cambodia (g 4/100 g diet) | 165.9 ± 8.9 |
| Propionyl L-carnitine (g 2/100 g diet) + Garcinia cambodia (g 4/100 g diet) | 155.5 ± 6.8 |

What is claimed is:

1. A method for reducing cholesterol in hypercholesterolaemia, comprising administering to a subject in need thereof an effective amount of a composition, wherein said composition comprises:
   (i) a first component selected from the group consisting of propionyl L-carnitine, and pharmaceutically acceptable salts of propionyl L-carnitine; and
   (ii) a second component selected from the group consisting of hydroxycitric acid, salts of hydroxycitric acid, and esters of hydroxycitric acid,
      wherein said composition comprises said second component and said first component in a weight ratio of from 1:1 to 1:2.

2. The method of claim 1, wherein said composition is orally administrable.

3. The method of claim 1, wherein said composition is parenterally administrable.

4. The method of claim 1, wherein said composition comprises calcium hydroxycitrate.

5. The method of claim 1, wherein said composition further comprises at least one ingredient selected from the group consisting of vitamins, mineral salts, antioxidants, and vegetable fibers.

6. The method of claim 1, wherein said composition is a solid.

7. The method of claim 1, wherein said composition is a semisolid.

8. The method of claim 1, wherein said composition is a liquid.

9. The method of claim 1, wherein said composition is a powder.

10. The method of claim 1, wherein said composition is in liposomic form.

11. The method of claim 1, wherein said composition is a tablet.

12. The method of claim 1, wherein said composition is a capsule.

13. The method of claim 1, wherein said composition is in a vial.

14. The method of claim 1, wherein said composition further comprises chromium.

15. The method of claim 1, wherein said pharmaceutically acceptable salt of propionyl L-carnitine is selected from the group consisting of propionyl L-carnitine chloride, propionyl L-carnitine bromide, propionyl L-carnitine orotate, propionyl L-carnitine acid aspartate, propionyl L-carnitine acid phosphate, propionyl L-carnitine fumarate, propionyl L-carnitine lactate, propionyl L-carnitine maleate, propionyl L-carnitine acid maleate, propionyl L-carnitine acid oxalate, propionyl L-carnitine acid sulfate, propionyl L-carnitine glucose phosphate, propionyl L-carnitine tartrate, and propionyl L-carnitine acid tartrate.

\* \* \* \* \*

UNITED STATES PATENT AND TRADEMARK OFFICE
CERTIFICATE OF CORRECTION

PATENT NO. : 6,217,898 B1
DATED : April 17, 2001
INVENTOR(S) : Cavazza

It is certified that error appears in the above-identified patent and that said Letters Patent is hereby corrected as shown below:

<u>Title page,</u>
Item [30], the Foreign Application Priority should read as follows:

-- [30] Foreign Application Priority Data

Dec. 15, 1995  (IT) ............................................. RM95A000824 --

Signed and Sealed this

Thirteenth Day of November, 2001

Attest:

NICHOLAS P. GODICI
*Attesting Officer*    *Acting Director of the United States Patent and Trademark Office*